United States Patent
Freeman

Patent Number: 5,830,496
Date of Patent: Nov. 3, 1998

[54] WOUND FILLER

[75] Inventor: Frank Freeman, Abaco, Bahamas

[73] Assignee: E.R. Squibb & Sons, Inc., Princeton, N.J.

[21] Appl. No.: 795,292

[22] Filed: Feb. 4, 1997

Related U.S. Application Data

[63] Continuation of Ser. No. 492,603, Jun. 20, 1995, abandoned, which is a continuation of Ser. No. 120,477, Sep. 13, 1993, abandoned.

[51] Int. Cl.$^6$ ..................................... A61L 15/00
[52] U.S. Cl. ......................... 424/445; 424/443; 424/446; 602/41
[58] Field of Search ................... 424/445, 443, 424/446; 602/41

[56] References Cited

U.S. PATENT DOCUMENTS

| | | | |
|---|---|---|---|
| 3,949,742 | 4/1976 | Nowakowski | 128/155 |
| 3,969,498 | 7/1976 | Catania | 424/28 |
| 4,231,357 | 11/1980 | Hessner | 128/156 |
| 4,563,184 | 1/1986 | Korol | 604/368 |
| 4,784,857 | 11/1988 | Berry | 424/449 |
| 4,793,337 | 12/1988 | Freeman et al. | 128/156 |
| 5,115,801 | 5/1992 | Cartmell | 602/48 |
| 5,238,685 | 8/1993 | Wren | 424/445 |

FOREIGN PATENT DOCUMENTS

| | | |
|---|---|---|
| 0 092 999 A2 | 11/1983 | European Pat. Off. |
| 0 160 569 A2 | 11/1985 | European Pat. Off. |
| 0 304 536 A2 | 3/1989 | European Pat. Off. |

*Primary Examiner*—D. Gabrielle Brouillette
*Attorney, Agent, or Firm*—John M. Kilcoyne; Theodore R. Furman, Jr.; Allen R. Kipnes

[57] ABSTRACT

A method of treating a wound comprising minimizing pressure on newly formed tissue around the perimeter of the wound by applying within the borders of the wound, a multi-layer laminate having a non-stretchable wound contact layer, a core layer comprising an absorbent material and a stretchable outer surface layer.

7 Claims, 2 Drawing Sheets

WOUND FILLER

This is a continuation of application Ser. No. 08/492,603, filed Jun. 20, 1995, now abandoned, which is a continuation of application Ser. No. 08/120,477, filed Sep. 13, 1993, now abandoned.

FIELD OF THE INVENTION

The present invention is directed to improved wound dressings having superior absorption and dimensional stability in a horizontal plane i.e., along the vertical x and y axes of the dressing. Two of the problems encountered in wound care treatment is keeping a wound clean and facilitating healing. The outer layer of human skin performs a protective function, which acts as a barrier to infection and as a means of regulating the body's heat and fluids between the body and the environment. When the skin is torn, punctured or damaged by being abraded, burnt or lacerated, this skin's protective function has been reduced. Such areas are conventionally protected by the application of a wound dressing, which covers the wound and acts to promote a moist healing environment.

In wound treatment it is desirable to provide a wound dressing which will maintain the desired moist environment while preventing scab formation. In addition, the wound dressing must also permit removal of wound fluid which can build up between the dressing and the skin. A build up of fluid between the wound and the dressing can cause separation of the dressing from the skin. Separation of the dressing from the skin can increase the possibility of the wound being contaminated by microorganisms which can cause infection.

Wound dressings are particularly important in the care of ulcers, particularly those that arise in the bedridden patients. One of the major problems in the health care of elderly patients is the treatment of ulcers, and pressure sores. Pressure sores and ulcers are often causes of pain, suffering, and infectious complications. The dressing of the present invention has particular application in the treatment of ulcers and other wounds.

BACKGROUND

One type of dressing that has been commonly used as a wound dressing is an occlusive hydrocolloidal dressing. These dressings maintain a moist environment for the wound that is the ideal condition for granulation and healing. An hydrocolloidal dressing can also be useful in maintaining a suitable pH of the wound environment. The preferred pH is slightly acid, about a pH of 6.0. The slightly acid environment ensures that the cells responsible for the formation of granulation tissue, including myofibroblasts, endothelial cells, macrophages and platetets are functional.

U.S. Pat. No. 3,969,498 to Catania describes hydrocolloidal dressings which are plasma soluble and which form an artificial eschar at the wound site. These dressings are comprised of a hydrophilic foam of dextran polymer. One problem with hydrocolloidal dressings in the past has been the odor generated by the dressing. Another problem with hydrocolloidal dressings has been their tendency to disintegrate in the presence of excess fluid.

Since many wounds exude fluids during the healing process one of the primary purposes of the dressing is to absorb excess fluid. In absorbing excess fluid conventional bandages have a strong tendency to expand during the absorption process. This expansion is three dimensional. As a result the dressing volumetrically expands in both the vertical and horizontal planes i.e. the x, y and z axes. As used herein the x and y axes of a bandage are analogous to the length and width of a bandage while the z axis is analogous to the height or thickness. Vertical volumetric expansion of the wound dressing generally does not present any problems during patient care. Horizontal expansion, however, is a different situation. Dressings must be periodically changed and as the wound heals the wound generally reduces its horizontal dimensions thus, becoming smaller and smaller. As a result, as healing progresses, conventional bandages that expand horizontally place undesirable pressure on the newly formed tissue thus creating problems in patient care in particular delays in healing. Specifically the horizontal expansion of the dressing due to fluid absorption coupled with the wounds natural gradual reduction in its overall dimensions causes the bandage places pressure on the wound surround and there is a tendency for the bandage to push the wound surround outwardly. In addition, horizontal expansion of the dressing increases the risk of the dressing becoming adhered to the wound. Adherence of the dressing to the wound can cause the wound to become re-injured when the dressing is disturbed such as being removed for changing. One material that is commonly used for wound dressings that has been found to be particularly susceptible to this type of expansion in all directions are dressings which are based on Kraton.

As a result, there is a need for dressings having superior absorption coupled with dimensional stability in the horizontal plane, i.e. x and y axes. Superior absorption reduces the need for unnecessary dressing changes thereby reducing the possibility of disturbing the moist wound healing environment generated by the dressing. In addition costs are reduced and caregivers time is freed for other tasks and responsibilities.

It is an object of the present invention to provide an improved wound dressing having dimensional stability in the horizontal plane.

It is also an object of the present invention to provide an improved wound dressing that has superior absorption of wound exudate.

It is a further object of the present invention to provide an improved wound dressing that promotes wound healing.

These and other objects will be readily apparent from the summary of the invention drawings and detailed description which follow.

SUMMARY OF THE INVENTION

The improved dressing of the present invention is a multilayer laminate that can be either in the form of a film, sheet, tape or rope. This multilayer laminate has been found to provide improved dimensional stability in the horizontal plane. That is, the dressing of the present invention has a reduced tendency to expand along the x and y axes compared to z or vertical axis. In one embodiment of the invention, the multi-layer laminate is provided with discrete pockets formed in the laminate. The presence of these pockets reduces the tendency for horizontal expansion even further. These pockets also permit the dressing to be trimmed to any desired shape to conform to the wound's dimensions without the material of the laminate becoming separated from the remainder of the laminate.

The multilayer laminate of the present invention preferably has at least three layers, two outer layers and a center core layer. The first outer layer is a wound contact layer comprised of a high wet strength material. The core or an intermediate layer is comprised of a superabsorbent material, a hydrocolloid material, a hydrophilic fiber or combinations thereof. The second outer layer or top surface layer is comprised of a material that is porous and possesses stretch characteristics.

The invention, accordingly, comprises the apparatus possessing the construction, combination of elements and arrangement of parts which are exemplified in the following detailed disclosure. For a fuller understanding of the nature and objects of the invention reference should be made to the following detailed description taken in connection with the accompanying drawings.

DETAILED DESCRIPTION OF THE INVENTION

Figure 1:
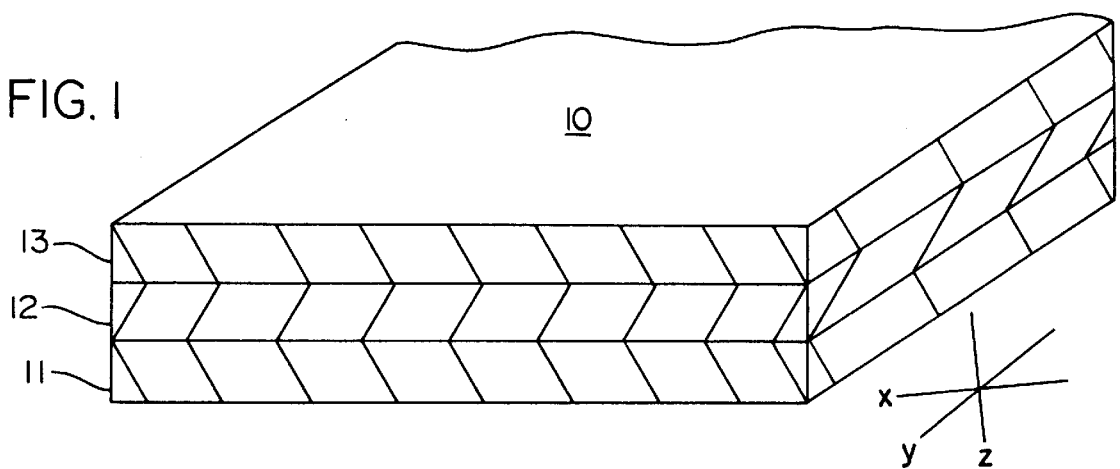
FIG. 1 is a perspective view of the wound dressing of the present invention in the form of a sheet.
Figure 2:
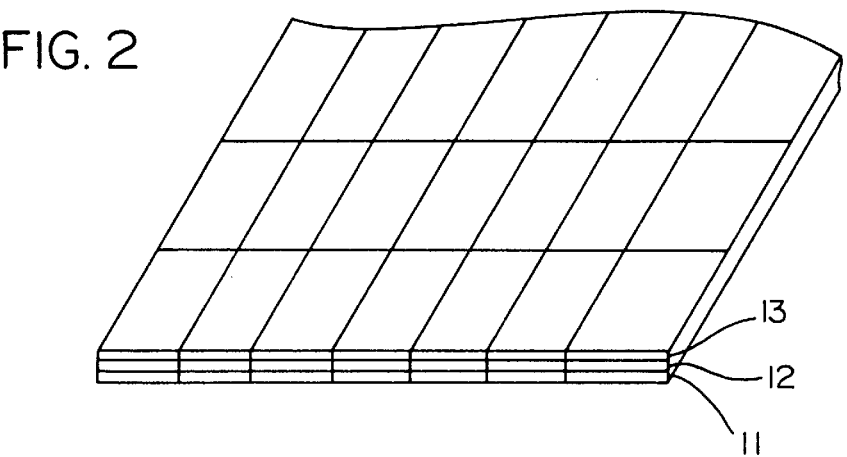
FIG. 2 is a perspective view of the sheet of FIG. 1 showing the pockets.
Figure 3:
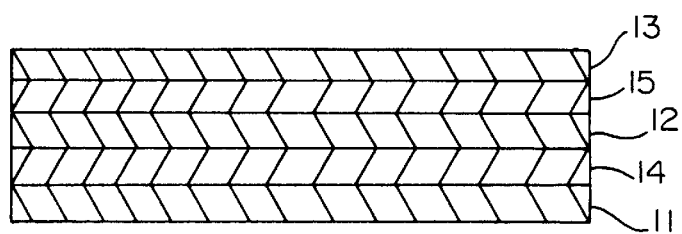
FIG. 3 is a side view of the wound dressing of FIG. 1 having additional layers.
Figure 4:
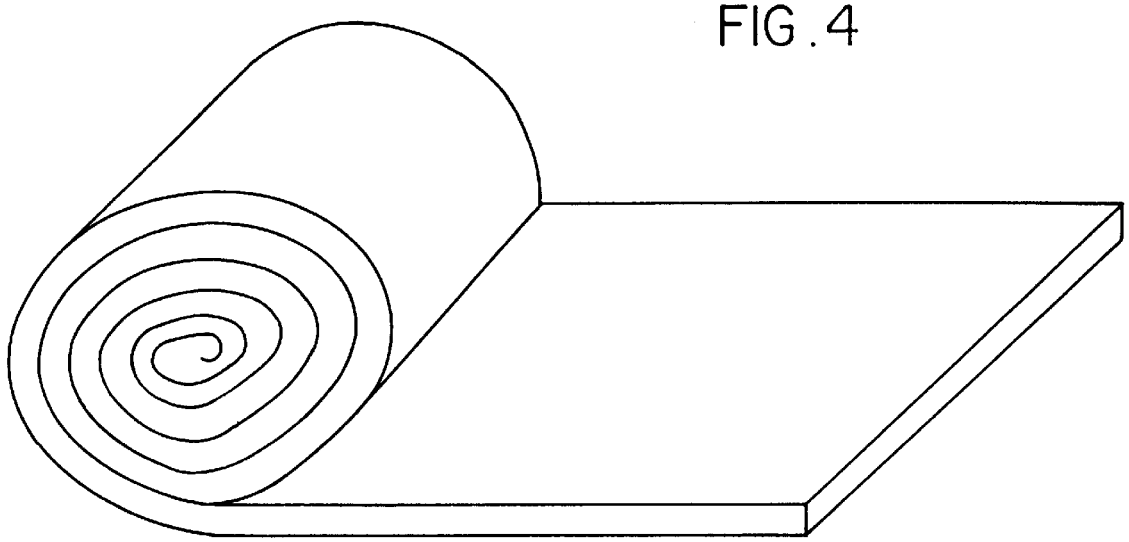
FIG. 4 is a perspective view of the sheet of FIG. 1 in the form of a tape.
Figure 5:
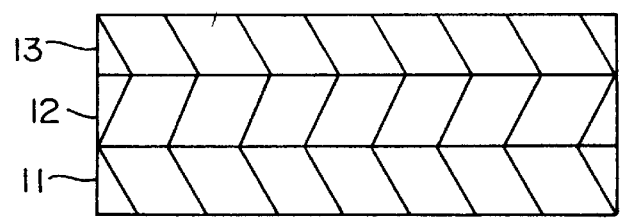
FIG. 5 is a end view of the tape of FIG. 3.

The multilayer sheet 10 that comprises the dressing of the present invention is generally comprised of three layers although additional layers may be present in the laminate. The first layer is a wound contact layer or bottom surface layer 11. The wound contact layer is preferably comprised of a material having a high wet strength such as a non-woven material. The non-woven material composition may be, for example, a mixture of fibers predominantly of short, cellulosic fibers such as wood pulp fibers or cotton linters with the remainder of the mixture being textile length fibers. The non-woven may also be formed from polyester, polyethylene, nylon, rayon or other non-woven materials including hydrocolloid/polysaccharide adsorbents. Preferred polyolefin materials for the wound contact layer may also include ethylene vinyl acetate, low density polyethylene, linear low density polyethylene, ultra low density polyethylene or very low density polyethylene, i.e., linear low density polyethylenes with densities below about 0.910 g/cm$^3$. Also suitable are polypropylenes, Saran films such as vinylidene chloride copolymers of vinyl chloride or methyl acrylate and others such as methyl methacrylate copolymers. Suitable polyesters include polyethylene terepthalate.

The first layer or wound contact layer is preferably a material with little or no stretch characteristic. In addition, the material selected should be capable of remaining lint free on its surface.

The wound contact layer may also contain a hydrocolloid which are known agents for promoting wound healing. The preferred hydrocolloids may include any water soluble gum such as pectin, gelatin, carboxymethylcellulose (CMC), sodium/calcium alginate fibers, polysaccharides and the like. The hydrocolloid may also comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly (alkyl phosphonates), partially hydrolyzed polyacrylamides (e.g., poly (N-N-dimethyl acrylamide), sulfonated polystyrene, or a class of poly (alkylene oxide). These highly hydrophilic synthetic polymers may be modified by other chemical treatments such as cross-linking or hydrolysis. Further examples known in the art are the non-ionic hydrophilic polymers such as polyoxyethylene, polyoxypropylene and mixtures thereof which have been suitably cross-linked, either chemically or by irradiation. Still another more recent type is a derivative of isobutylene-maleic anhydride copolymer. The wound contact layer may also contain additional materials such as antibiotics or growth factors and silver sulfadiazine or other antibacterial products. The hydrocolloid may be present in the film, either with or without accelerators to promote release, such as surfactants, etc.

Hydrophilic polymers formed from water-soluble acrylate monomers, such as sodium, potassium, ammonium (or combinations of cations) acrylate may be placed on the web by spraying or otherwise placing a solution thereon followed by polymerization and cross linking, for example by irradiation.

In one embodiment of the present invention, wound contact layer may be a perforated film of a polymeric material which has been coextruded with a hydrocolloidal substance to form a blend. The wound contact layer can be of any suitable polymeric material, however, when hydrocolloids are included in the layer by coextrusion the preferred polyolefin is an ethylene vinyl acetate. One suitable EVA is Union Carbide's Natural 7 and another EVATANE 1020 VN5 or 1080 VN5. The EVA preferably has a vinyl acetate (VA) content of about 15 to 28% more preferably about 18%. While it would be possible under certain processing conditions to use other polyolefins besides EVA, many of the other polyolefinic materials currently available have a melting temperature higher than about 105° C. At temperatures higher than about 105° C. the hydrocolloid has a tendency to degrade. Thus, the polymeric material should have a melting temperature about 105° C. or below.

The hydrocolloidal containing wound contact layer can be formed by any suitable process. One process that has been found to be suitable is the use of a twin screw extruder to extrude granulated EVA. The extrudate is then re-extruded and the hydrocolloid material is mixed into the EVA in a section of the screw. The EVA containing hydrocolloidal materials is then extruded to form a film which can be laminated or adhered to the remainder of the dressing by any conventional process.

It is preferred that the wound contact layer be perforated to provide a fluid path for the wound fluids. The perforations may be formed by any suitable means. One such means of perforating the film is by passing the film over a heated roll or where the holes are punched into the film mechanically.

Another method of perforating the film is by extruding the film, embossing it on a roll and biaxially orienting the film. It is preferred that there be at least 40 perforations to a square inch to provide a good area for absorption.

In an alternate embodiment of the invention, the hydrocolloid can be coated onto the wound contact layer. In one method of applying the hydrocolloidal material, the hydrocolloidal material (HCD) can be applied by coating a thin perforated film with or 2 or 3% solution of the HCD in water. When an aqueous solution of HCD is being applied to the thin perforated film the thin film may be treated by corona discharge to promote adhesion. In an alternative embodiment, a solution such as a 10% suspension of HCD in a gelled mineral oil petroleum jelly, a suppository base such as Huls-Witespol Softisan or other suitable carrier may be used. The suppository base is generally a vegetable fatty acid having a C10–C18 length carbon chain.

Over the wound contact layer is an intermediate layer 12 this intermediate or core layer may be adhered directly to the wound contact layer or additional layers may be interposed between the two layers. The intermediate layer is generally a layer of a superabsorbent material hydrocolloid or a hydrophilic fiber or combination thereof.

The material of the absorbent layer 12 can be a fabric, foam, fiber or the like which is capable of both absorbing fluids and bonding to the wound contact layer 11. This absorbent material can be the traditional pulp products either with or without a superabsorbent material.

The absorbent layer can be any of the materials used in wound care particularly materials rendered superabsorbent including spun-laced polyester, non woven materials bonded to polyester film (such as Kendall's Novenette). Typical of these include, but are not limited to, natural and synthetic polymeric adsorbents, hydrocolloids/polysaccharide adsorbents, cellulosic adsorbents, i.e., cotton, rayon, wood cellulose, superabsorbents in the following forms: sheets, fibers, adhered to any web by means of steam, water, gel forming fluid adhesive dressings, wool, cotton, lint, superabsorbents, i.e., water-swellable polymer—typically in the form of fiber or flock materials. Specific suitable materials are the composite air laid superabsorbent pad (dry forming process and the superabsorbent fiber flock SAFF) sold by Hanfspinnern Steen & Company; Polypropylene fibre mat impregnated with SAP/HCD alone or in combination are also suitable. The superabsorbent may be a delayed released superabsorbent.

Superabsorbent webs can be formed by slightly moistening or misting a web, of non-woven materials and other types including:

Carded Webs—cotton, rayon, polyethylene, wool

Random Webs—cotton, rayon, polyethylene, polyester, wool

Spun-laced webs—polyester, polypropylene, polyethylene

Tissues—single ply or multiple—creped and uncreped

Delnet, a product of Applied Extrusion Technologies which consists of a range of materials manufactured from polyethylene or polypropylene using extrusion embossing and orientation processes may also be used.

These materials may be rendered superabsorbent by applying a powdered superabsorbent and running the web during a dry oven or heating the roll. The powder adjacent to the moistened web will become tacky and adhere to the adjacent material (fiber, surface), and the loose powder would then be vacuumed off.

In addition, superabsorbent powder can be sandwiched between non-woven webs/paper and subjected to moist steam which would make the superabsorbent tacky which would then stick to adjacent surfaces. They can also be heat bonded. The sandwiched superabsorbent and web would then be dried creating a two ply web with superabsorbent between them. The above structure could be embossed to improve functional features. The superabsorbent material present can be in an intermittently dispersed form in the web and is generally a water insoluble but water swellable polymeric substance capable of absorbing water in an amount which is at least 10 times the weight of the substance in its dry form.

The superabsorbent material in the core layer may also be present for example in the form of a plurality of particles or globules of superabsorbent material disposed in a random arrangement throughout the layer. Preferably the superabsorbent particles or globules are of a size and spacing so that they do not interfere with the absorption of wound fluid by adjacent particles upon expansion.

In one type of superabsorbent material, the particles or fibers may be described chemically as having a backbone of natural or synthetic polymers with hydrophilic groups or polymers containing hydrophilic groups being chemically bonded to the backbone or an intimate admixture therewith. Included in this class or materials are such modified natural and regenerated polymers as polysaccharides including, for example, cellulose and starch and regenerated cellulose which are modified being carboxyalkylated, phosphonoalkylated, sulphoalkylated or phosphorylated to render them highly hydrophilic. Such modified polymers may also be cross-linked to improve their water-insolubility.

These same polysaccharides may also serve, for example, as the backbone onto which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain. The preferred hydrophilic chains are hydrolyzed polyacrylonitrile chains and copolymers of polyacrylamide and polysodium acrylate.

The top or outer surface layer should be a porous material and stretchable possess stretch characteristics either uniaxially or biaxially i.e. stretchable either in one horizontal direction or two. In addition, the top layer must be capable of being sealed to the intermediate layer. Suitable sealing methods include heat, ultrasonic and radiofrequency sealing. One preferred material is the stretch bonded laminate SBL sold by Kimberly Clark. Other suitable materials can be the family of stretch fabrics based on DuPont's lycra.

Figure 7:
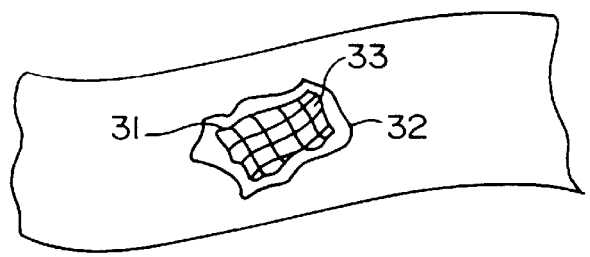
FIG. 7 is the dressing of the present invention cut to shape to fit a wound.

The previously described materials are joined together by suitable heat or ultrasonic sealing methods so as to produce a sandwich construction with sealed edges. Various shapes, circles, ellipsoids, tapes, ropes can be formed and cut out using heat sealing and cutting techniques. It is desired to cut shapes, as is often the case as many wounds, such as leg ulcers, are irregular in shape, then the laminate is heat sealed using a patterned die to produce a multiplicity of small pocket areas, each sealed around its circumference. This enables irregular shapes to be cut without significant loss of material from the inner material of the sandwich construction. See FIG. 7 where the dressing 31 is cut to the shape of the wound 32. The pockets 33 hold the dressing together to prevent horizontal expansion. The multiplicity of small pocket areas may be formed by sealing the layers together by any suitable means such as heat sealing, heating ultrasonic heating etc. In addition, the pockets may be formed by stitching or sewing the layers.

Figure 6:
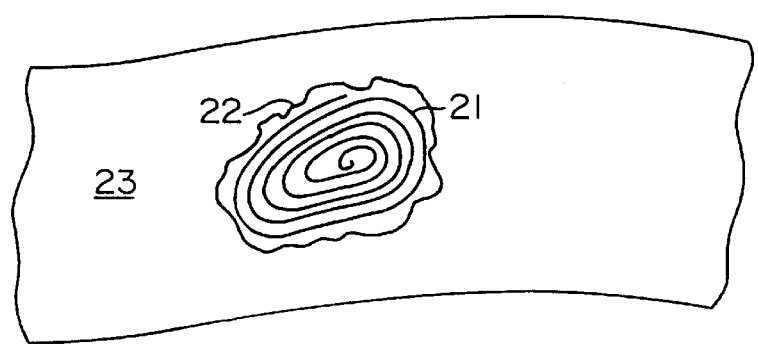
FIG. 6 is the dressing of the present invention in the form of a rope.

Additional layers may also be present in the dressing such as additional core layers 14 and adhesive layers 15 and to increase absorption of wound fluids. As seen in FIG. 6 the dressing of the present invention is in the form of a rope 21 placed onto the wound 22 on a limb of the body.

I claim:

1. A method of treating a wound comprising minimizing pressure on newly formed tissue around the perimeter of a wound by applying solely within the borders of the wound, a multi-layer laminate having a non-stretchable wound contact layer, a core layer comprising an absorbent material and a stretchable outer surface layer, said laminate having an x axis and a y axis corresponding to the length and width of said laminate and a z axis corresponding to the thickness of said laminate, said laminate expanding along the z axis to a greater extent than the x and y axis when the laminate is contacted with a fluid.

2. The method of claim 1 wherein the laminate has seals that form a multiplicity of pocket areas which provide dimensional stability in the x and y axis.

3. The method of claim 1 wherein the wound is a pressure sore or ulcer.

4. The method of claim 1 wherein said wound contact layer is a non-woven material and includes a hydrocolloid, said core layer is a fabric, a foam or a spun laced polyester, and said laminate has sealed edges.

5. A method of treating a wound comprising minimizing pressure on newly formed tissue around the perimeter of a wound by applying solely within the borders of the wound, a multi-layer laminate having a non-stretchable, biaxially oriented wound contact layer having at least 40 perforations per square inch, a core layer of an absorbent material and an outer surface layer, said laminate having a plurality of seals forming pocket areas to provide dimensional stability in the horizontal plane of the laminate.

6. The method of claim 5 wherein the wound is a pressure sore or ulcer.

7. The method of claim 5 wherein said wound contact layer is a non-woven material and includes a hydrocolloid, said core layer is a fabric, a foam or a spun laced polyester, and said laminate has sealed edges.

\* \* \* \* \*